US012217858B2

(12) United States Patent
Tran et al.

(10) Patent No.: US 12,217,858 B2
(45) Date of Patent: Feb. 4, 2025

(54) HEALTHCARE CHARGE CAPTURE AND PRIORITIZATION SYSTEM AND METHOD

(71) Applicant: DPACC Administrative Services, LLC, Dallas, TX (US)

(72) Inventors: Tung Tran, Southlake, TX (US); Shibu Thomas, Plano, TX (US); Amit Mann, Lewisville, TX (US); Melissa Stewart, Hurst, TX (US); Leia Oh-Spradling, Richardson, TX (US); Stephanie Fargo, Hurst, TX (US)

( * ) Notice: Subject to any disclaimer, the term of this patent is extended or adjusted under 35 U.S.C. 154(b) by 129 days.

(21) Appl. No.: 18/059,940

(22) Filed: Nov. 29, 2022

(65) Prior Publication Data
US 2023/0091011 A1 Mar. 23, 2023

Related U.S. Application Data

(62) Division of application No. 16/743,625, filed on Jan. 15, 2020, now Pat. No. 11,972,860.

(51) Int. Cl.
*G16H 40/20* (2018.01)
*G16H 15/00* (2018.01)

(52) U.S. Cl.
CPC .............. *G16H 40/20* (2018.01); *G16H 15/00* (2018.01)

(58) Field of Classification Search
CPC ........ G16H 40/20; G16H 15/00; G06Q 10/10; G06Q 30/04; G06Q 40/08
See application file for complete search history.

(56) References Cited

U.S. PATENT DOCUMENTS

| 2007/0026211 A1* | 2/2007 | Rabtor | B32B 27/32 |
| | | | 428/522 |
| 2012/0166212 A1* | 6/2012 | Campbell | G16H 50/20 |
| | | | 705/2 |
| 2015/0379241 A1* | 12/2015 | Furst | G16H 10/60 |
| | | | 705/3 |

* cited by examiner

*Primary Examiner* — Maroun P Kanaan
(74) *Attorney, Agent, or Firm* — Kearney, McWilliams & Davis, PLLC; William Yarbrough

(57) ABSTRACT

A healthcare charge capture and prioritization system for assisting healthcare providers with capturing their procedures and prioritizing code selection for claim submission is presented. The system can analyze healthcare claim-related data for ranking and ordering Current Procedural Technology (CPT) and International Statistical Classification of Diseases and Related Health Problems (ICD) codes to reduce the utilization of additional processing resources and network utilization from repeated system denials. Additionally; the present disclosure can generate and track analytics relevant to a patient encounters and provider action, It is an object of the invention to provide a system for processing and managing patient interactions, processing and managing healthcare-related charge entry, processing and prioritizing healthcare-related procedure technology codes, and processing and prioritizing disease and related health problem codes.

17 Claims, 8 Drawing Sheets

FIG. 4

HEALTHCARE CHARGE CAPTURE AND PRIORITIZATION SYSTEM AND METHOD

BACKGROUND OF THE INVENTION

1. Field of the Invention

The present invention generally relates to healthcare charge capture systems and more particularly to charge capture systems having prioritization algorithms for claim submission.

2. Background of the Invention and Description of the Prior Art

Generally speaking, charge capture systems provide a means for service providers to track and manage interactions with patients. However, with multiple providers (both physicians and Advanced Practice Providers or "APPs") engaging multiple patients at multiple facilities over the course of a day, charge entry can get put on the backburner, potentially resulting in lost revenue if the charges are not billed timely or at all.

Additionally, charges for procedures can be as subjective as the review of the charges for payment. Two mechanisms have been standardized in an attempt to remove the subjectivity of procedures and disease states: Current Procedural Technology (CPT) codes and International Statistical Classification of Diseases and Related Health Problems (ICD) codes. In short, the CPT and ICD codes tell the payer that a particular patient at a particular healthcare facility exhibits certain symptoms (represented by the ICD codes) and that the providers performed certain procedures to treat those symptoms (represented by the CPT codes). These codes tell the insurance payer what procedures the healthcare provider would like to be reimbursed for.

However, when claims, having ICD codes are submitted to the payer for approval or denial, codes that although related, are seemingly not required for a particular disease state can be denied. If a claim leads with these ancillary procedure codes, the claim could be denied before the essential procedure codes are reviewed. Similarly problematic is the submission of a CPT code for a lower paying procedure, when a higher paying procedure is available-such as procedures that are performed by physicians, which generally pay at higher rates that procedures performed by APPs.

SUMMARY OF THE INVENTION

The present disclosure achieves technical advantages as a healthcare charge capture and prioritization system for assisting healthcare providers with capturing their procedures and prioritizing code selection for claim submission. The present disclosure solves the technological problem of applying a data optimization algorithm to healthcare charge-related data to generate an optimized electronic claim and healthcare charge analytic system. The present disclosure improves the performance of the system itself by analyzing healthcare claim-related data for ranking and ordering Current Procedural Technology (CPT) and International Statistical Classification of Diseases and Related Health Problems (ICD) codes to reduce the utilization of additional processing resources and network utilization from repeated system denials. Additionally, the present disclosure can generate and track analytics relevant to patient encounters and provider action. In contrast, traditional charge capture systems simply reroute existing data, resulting in haphazard claim submissions that do not advance the claims process, but instead simply add to the strain on an already overspent system. Advantageously, the present disclosure enhances the healthcare claim process by implementing algorithms that capture and weigh various claim data to create a database of charge data analytics that can streamline charge capture and claim generation functionality for the healthcare provider. Importantly, the present disclosure can save a provider time, increase revenue, provide a platform for previously uncaptured data analytics, and identify areas for improvement.

It is an object of the invention to provide a system for processing and managing patient interactions. It is a further object of the invention to provide a system for processing and managing healthcare-related charge entry. It is a further object of the invention to provide a system for processing and prioritizing healthcare-related procedure technology codes. It is a further object of the invention to provide a system for processing and prioritizing disease and related health problem codes.

These and other objects are provided by the following embodiments.

In one embodiment, a system for processing and managing patient interactions, can include: a system processor running a patient interaction module configured to, in order to process and manage patient interactions and notifications: receive login credentials from a user device for a user over an encrypted network; receive patient data for a plurality of patients at a first location from an electronic health record system for patients assigned to the user for a predetermined time period over an encrypted network; determine a number of patient encounters for the user for the predetermined time period and generate an indication of the number of patients seen and unseen, and a progress bar representing a completion percentage of the number of patients seen for display on a user device; generate a notification indicating those patients having outstanding encounters for display on the user device; generate a patient record for each patient using at least a portion of the received patient data, including an encounter indicator, indicating whether the patient has been seen by a physician, seen by an advanced practice provider, or needs to be seen, and a clinical indicator, generate a patient profile having the encounter indicator, at least a portion of the received patient data, a summary of the patient's condition, and a follow-up task listing for display on the user device; and provide a user interface for modifying the patient profile to the user device over an encrypted network.

In another embodiment, a Current Procedural Technology (CPT) prioritization platform, can include: a server having a system processor running a healthcare charge entry module configured to, in order to process and prioritize a CPT code: receive CPT information for a patient for a predetermined period, including provider information and patient information; determine whether the provider for each received CPT is a physician or APP; determine whether multiple CPTs occurred over the predetermined period; associate, via the server, a work relative value unit (RVU) for each received CPT; compare the CPT RVUs, via the server, to rank the CPT RVUs over the predetermined period; if there is a tie for the highest CPT RVU value, select a physician CPT with the highest RVU for claim submission, otherwise, select a CPT with the highest RVU for claim submission; and generate a claim for the predetermined period using the selected CPT.

In another embodiment, an International Statistical Classification of Diseases and Related Health Problems (ICD) code prioritization system, can include: a server having a system processor running a healthcare charge module configured to, in order to process and prioritize disease and related health problem codes: receive an approval or rejection of one or more ICD codes in the submitted claim; if an ICD code is approved, increment an ICD rank for the approved ICD code and increment an approval count, if an ICD code is denied, decrement the ICD rank for the denied ICD code and increment a denial count; store the ICD rank, the incremented count, and a timestamp of the approval or disapproval for the received approval or rejection; retrieve a history of the approved ICD code for a predetermined time frame; if a number of approved ICD codes surpasses a first threshold, increment the ICD rank for the approved ICD code, otherwise, analyze the ICD code approval amount; if the ICD code approval amount surpasses a second threshold, increment and store the ICD rank for the approved ICD code, otherwise, store the ICD code rank.

BRIEF DESCRIPTION OF THE DRAWINGS

FIG. 4 illustrates a view of a patient profile, in accordance with one exemplary embodiment of the present disclosure;

DETAILED DESCRIPTION OF THE INVENTION

The preferred version of the disclosure presented in the following written description and the various features and advantageous details thereof, are explained more fully with reference to the non-limiting examples included in the accompanying drawings and as detailed in the description, which follows. Descriptions of well-known components have been omitted so to not unnecessarily obscure the principle features described herein. The examples used in the following description are intended to facilitate an understanding of the ways in which the disclosure can be implemented and practiced. Accordingly, these examples should not be construed as limiting the scope of the claims.

Figure 1:
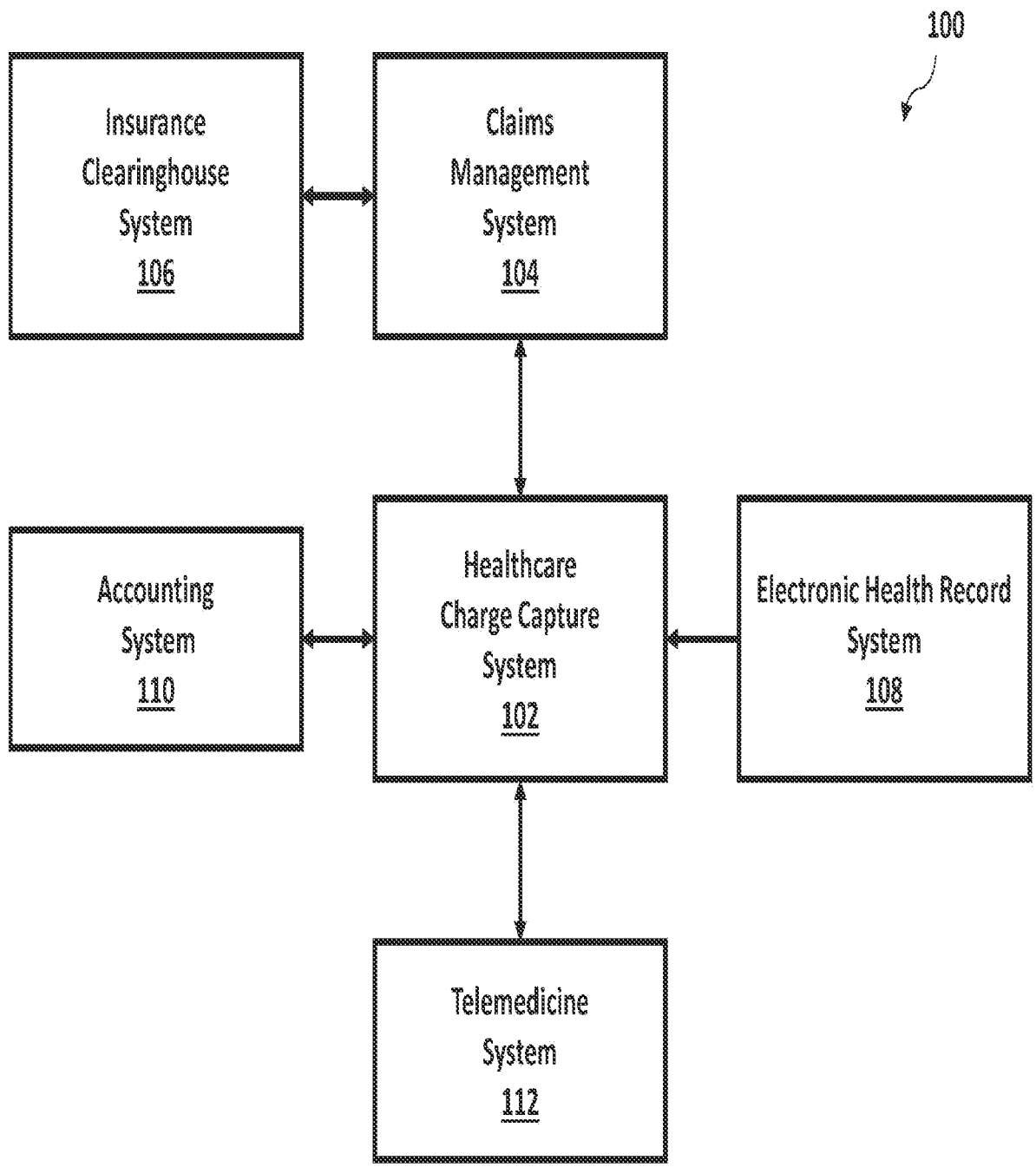
FIG. 1 illustrates a healthcare system network diagram depicting system components related to a healthcare charge capture and prioritization system, in accordance with one exemplary embodiment of the present disclosure.

FIG. 1 illustrates a healthcare system network diagram 100 depicting system components related to a healthcare charge capture and prioritization system (CCS) 102, in accordance with one exemplary embodiment of the present disclosure. The healthcare system network 100 can include a healthcare charge capture system 102, a claims management system 104, an insurance clearinghouse system 106, an electronic health record system 108, an accounting system 110, and a telemedicine system 112.

The aforementioned system components 102, 104, 106, 108, 110, and 112 can be communicably coupled to each other via the Internet, intranet, or other suitable network. The communication can be encrypted, unencrypted, over a VPN tunnel, or other suitable communication means. The Internet can be a WAN, LAN, PAN, or other suitable network. The network communication between the system components 102, 104, 106, 108, 110, and 112, can be encrypted to ensure HIPAA compliance using PGP, Blowfish, AES, 3DES, HTTPS, or other suitable encryption. The network communication can occur via application programming interface (API), health level 7 (HL7) standard, ANSI-X12, Ethernet, Wi-Fi, Bluetooth, or other suitable communication protocol. Additionally, third party databases can be operably connected to the system components 102, 104,106, 108, 110, and 112.

The claims management system 104 can be a server or other suitable component configured to receive a claim from CCS 102 via open API or HL7. Healthcare claims management software can be used to streamline medical claims' processing and billing workflow. Healthcare claims management software can be sold either as standalone products or bundled within medical billing software, revenue cycle management software, or comprehensive medical practice management software. Payers, healthcare providers, and insurance providers typically use healthcare claims management system 104. The systems can be configured to either push or pull data between CCS 102 and the claims management system 104. The claims management system 104 can create an electronic file (i.e., a claim) known as an ANSI-X12 837 file. This file can be transferred to an insurance clearinghouse system 106.

Insurance clearinghouse system 106 can be a server or other suitable component operably coupled to claims management system 104 via the network. Insurance clearinghouse system 106 can function as an intermediary between a provider and a payer. The payer can be an insurance company, or other suitable entity. Insurance clearinghouse system 106 can review a submitted claim claim for errors, and finding none, can transmit the electronic claim over an encrypted network to the payer. The claim is then either approved or denied by the payer, in which an approved claim generates a payment of services to the provider, and a denied claim may require additional information to procure processing.

Electronic health record system (EHR) 108, a/k/a electronic medical record (EMR), can be a server or other suitable component configured to provide a combination of patient demographics, patient records, length of stay, chart review, insurance information, and order management, among others, to the CCS 102. This EHR/EMR platform integrates clinical and revenue cycle management systems to track invoices and payments via a patient account number or other suitable identifier. A patient can have a barcode on a wrist band, RFID, ID card, or other suitable indication of his or her account number. The CCS 102 can pull data from the EHR/EMR system 108 via API, HL7, or other suitable connection.

Accounting system 110 can be a server or other suitable component. Accounting system 110 can keep track of the cost per encounter, and other metrics related to the provider's services and billings.

Telemedicine system 112 can be a server or other suitable component providing patient related content to the provider, including streaming of audio, video, text, and other suitable content, Telemedicine system 112 can include a camera, microphone, or other suitable transducer to provide data to CCS 102.

Figure 2:
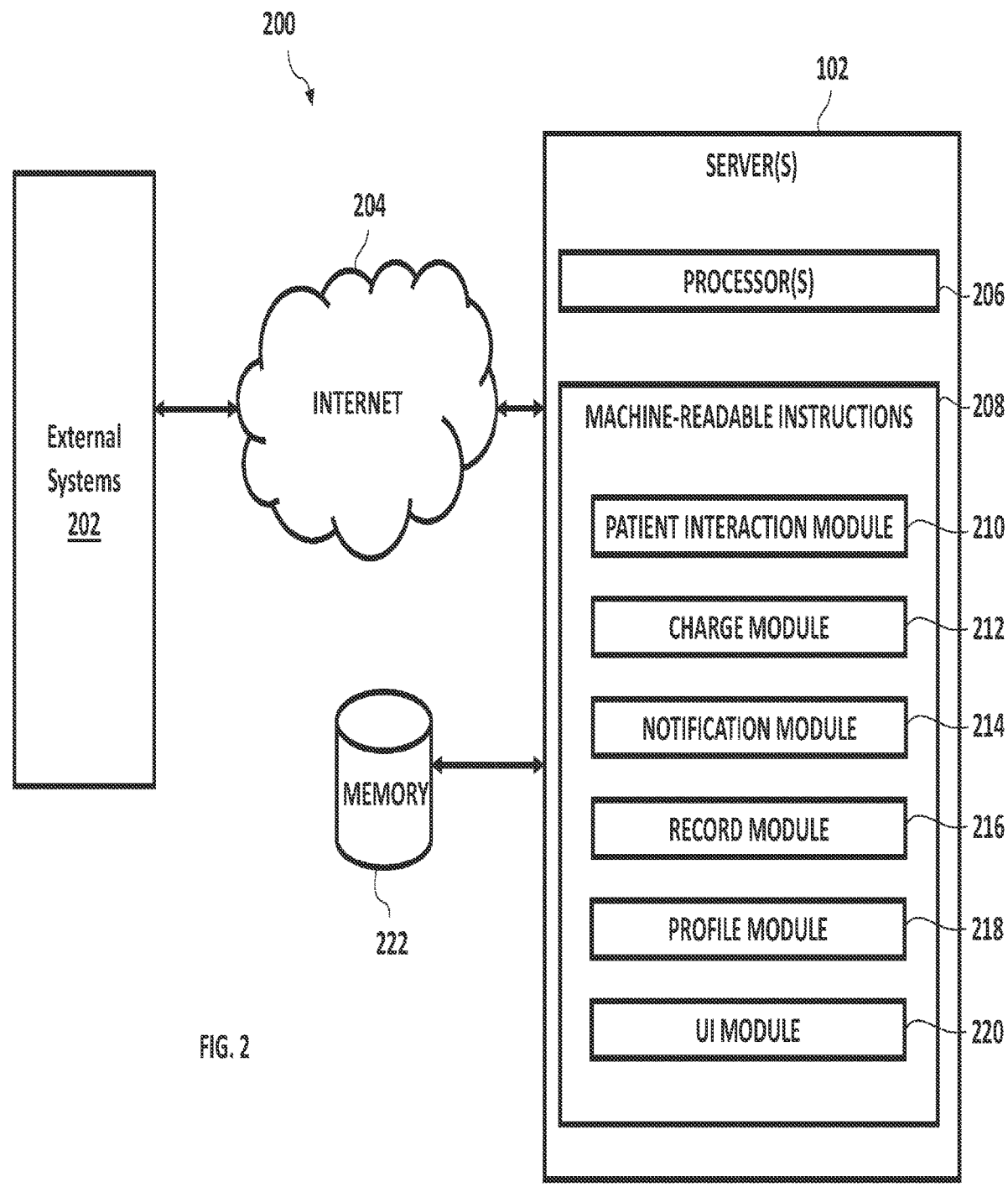
FIG. 2 illustrates a schematic view of a healthcare charge capture and prioritization system, in accordance with one exemplary embodiment of the present disclosure.

FIG. 2 illustrates a schematic view of a healthcare charge capture and prioritization system 102, in accordance with one exemplary embodiment of the present disclosure. Charge capture system 102 can include a server having one or more processors 206, a memory 222, machine readable instructions 208, including a patient interaction module 210, a charge module 212, a notification module 214, a record module 216, a profile module 218, and a UI module 220.

The CCS 102 can be communicably coupled to the Internet, intranet, or other suitable network. Such communication can be encrypted, unencrypted, over a VPN tunnel, or other suitable communication means. The Internet 204 can be a WAN, LAN, PAN, or other suitable network. The network communication between the system components 102, 104, 106, 108, 110, and 112, can be encrypted to ensure HIPAA compliance using PGP, Blowfish, AES, 3DES, HTTPS, or other suitable encryption. The network communication can occur via application programming interface (API), health level 7 (HL7) standard, ANSI-X12, Ethernet, Wi-Fi, Bluetooth, or other suitable communication protocol. Additionally, external systems, such as the system components 102, 104, 106, 108, 110, and 112, can be operably connected to the CCS 102 via the Internet 204. The server can be implemented in hardware, software, or a suitable combination of hardware and software therefor, and may comprise one or more software systems operating on one or more servers, having one or more processors 206, with access to memory 222. Server(s) can include electronic storage, one or more processors, and/or other components. Server(s) can include communication lines, or ports to enable the exchange of information with a network and/or other computing platforms. Server(s) can also include a plurality of hardware, software, and/or firmware components operating together to provide the functionality attributed herein to server(s). For example, server(s) can be implemented by a cloud of computing platforms operating together as server(s). Additionally, the server can include memory 222.

Memory 222 can comprise electronic storage that can include non-transitory storage media that electronically stores information. The electronic storage media of electronic storage may include one or both of system storage that is provided integrally (i.e., substantially non-removable) with server(s) and/or removable storage that is removably connectable to server(s) via, for example, a port (e.g., a USB port, a firewire port, etc.) or a drive (e.g., a disk drive, etc.). Electronic storage may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage may include one or more virtual storage resources (e.g., cloud storage, a virtual private network, and/or other virtual storage resources). Electronic storage may store machine-readable instructions, software algorithms, information determined by processor(s), information received from server(s), information received from computing platform(s), and/or other information that enables server(s) to function as described herein. The electronic storage can also be accessible via a network connection.

Processor(s) may be configured to provide information processing capabilities in server(s). As such, processor(s) may include one or more of a digital processor, an analog processor, a digital circuit designed to process information, an analog circuit designed to process information, a state machine, and/or other mechanisms for electronically processing information, such as FPGAs or ASICs. The processor(s) may be a single entity, or include a plurality of processing units. These processing units may be physically located within the same device, or processor(s) may represent processing functionality of a plurality of devices operating in coordination or software functionality.

The processor(s) can be configured to execute machine-readable instruction or learning modules by software, hardware, firmware, some combination of software, hardware, and/or firmware, and/or other mechanisms for configuring processing capabilities on processor(s). As used herein, the term "machine-readable instruction" may refer to any component or set of components that perform the functionality attributed to the machine-readable instruction component. This can include one or more physical processors during execution of processor readable instructions, the processor readable instructions, circuitry, hardware, storage media, or any other components.

The server can be configured with machine-readable instructions 208 having one or more functional modules. The machine-readable instructions 208 can be implemented on one or more servers, having one or more processors 206, with access to memory 222. The machine-readable instructions 208 can be a single networked node, or a machine cluster, which can include a distributed architecture of a plurality of networked nodes. The machine-readable instructions 208 can include control logic for implementing various functionality, as described in more detail below. The machine-readable instructions 208 can include a patient interaction module 210, a charge module 212, a notification module 214, a record module 216, a profile module 218, and a UI module 220.

The patient interaction module 210, can be configured to process and manage patient interactions and notifications, including receiving login credentials from a user device for a user over an encrypted network. The user (provider) can be a physician or an Advanced Practice Provider (APP). The patient interaction module 210 can receive patient data for a plurality of patients at a first location from an electronic health record system for patients assigned to the user for a predetermined time period over an encrypted network. Patient data can include patient demographics, patient records, length of stay, chart review, insurance information, and order management, among others. The first location can be a hospital, unit, wing, floor, section, or other suitable location. A patient can be assigned to a provider indefinitely or for a predetermined period of time. The predetermined period of time can be periodic, such as a day, or aperiodic, such as the duration of a treatment. The patient interaction module 210 can determine a number of patient encounters for the user (provider) for the predetermined time period and generate an indication of the number of patients seen and unseen, and a progress bar representing a completion percentage of the number of patients seen for display on a user device. The indication can be provided to a user device such as a computer, server, mobile device, or other suitable device, for display. The patient interaction module 210 can generate a notification indicating those patients having outstanding encounters for display on the user device. The notification can include a portion of a patient profile, including patient information.

As discussed in more detail below, the charge module 212 can implement a plurality of algorithms to prioritize charge entries for a given encounter or procedure, including a Current Procedural Technology (CPT) code prioritization algorithm and an International Statistical Classification of Diseases and Related Health Problems (ICD) code prioritization algorithm. The algorithms and associated thresholds can be programmable to suit a particular application, facility, or other requirement. The charge module 212 can correlate actual measured data with the calculated expected data to verify that the appropriate outcome is achieved. The measured data can include the time spent on each encounter/procedure, and time spent between each encounter/procedure, among others. The expected data can include predetermined data stored in the memory, including the designated time for each encounter/procedure, and the designated time between each encounter/procedure, among others. The charge module 212 can also track analytics related to a user, including charge reporting, and number of completed encounters/procedures, among other measurables.

The notification module 214, can be configured to send and receive messages related to patient interaction to and from the user device. The notification module 214 can generate one or more elements for display on the user device. The elements can provide additional information to the user related to patient encounters. For example, alerts can be generated by the notification module 214 and displayed on the user device, indicating outstanding encounters, a portion of the patient profile information, daily encounters entered or missing, encounter progress tracking, or other suitable information. Additionally, system symbols can be displayed on the user device to indicate task or patient status.

Advantageously, the record module 216 can generate a patient record for each patient using at least a portion of the patient data received by the server, including an encounter indicator, indicating whether the patient has been seen by a physician, seen by an advanced practice provider, or needs to be seen, and a clinical indicator. The encounter indicator can have a unique image, color, or other suitable symbol designating the particular status. The record module 216 can also include a user profile for the provider, indicating whether the provider is a physician, APP, or admin. The user profile can also indicate patient listing, credentialing, specialization, open encounters, time-to-encounter completion, and other provider-related information.

The patient profile module 218 can generate a patient profile formatted for display in a user device. The patient profile is stored locally in memory 222, such that CPT and ICD codes for patient encounters can be associated with a patient, for ease of recall. The profile can include a listing of encounters, including an encounter summary, an in-patient follow-up, the date of service, the location of the encounter, clinical indicators, the provider, the encounter indicator, at least a portion of the received patient data, a summary of the patient's condition, and a follow-up task listing for display on the user device among others. The patient profile can be a subset of the most relevant data from the patient record for a provider. However, the patient profile can be supplemented with additional relevant information not in the patient record.

The UI module 220 can provide a user interface for modifying the patient profile or patient record to the user device over an encrypted network. The UI module can generate data for presentation to the external systems 202 (user device) from any of the aforementioned modules 210, 212, 214, 216, 218, and 220. The UI module 220 can serve web pages or data, including via JavaScript, API, HTML, AJAX, RESTful services, or other suitable means. The UI module 220 can also provide a user interface for modifying the administrative portion of the CCS 102, including CPT and IDS ranking algorithms and thresholds. The UI module 220 can additionally provide a user interface for generating user reports and viewing analytics related to any element of the CCS 102.

Figure 3:
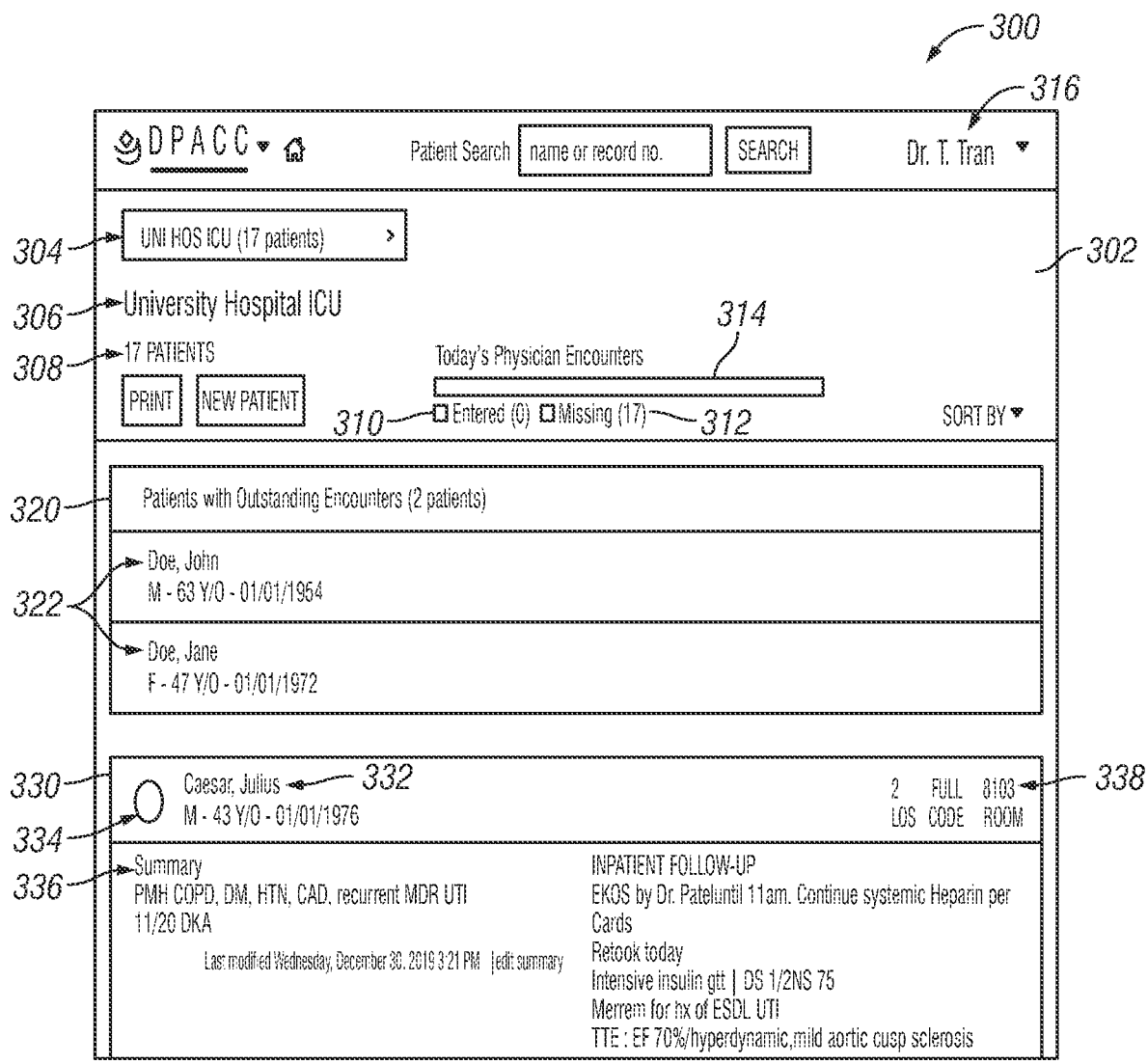
FIG. 3 illustrates a view of user interface related to patient encounters, in accordance with one exemplary embodiment of the present disclosure.

FIG. 3 illustrates a view of user interface 300 related to patient encounters, in accordance with one exemplary embodiment of the present disclosure. The patient encounter interface 300 can receive data from the UI module 220 to access and display data from any module of CCS 102, including the patient interaction module 210, profile module 218, and notification module 214. A first banner 302 is displayed across the top of the user interface. A user can access the system by providing valid credentials via a login, including a username and password, biometrics, multi-factor authentication, or other suitable credential. The name of the active user, as well as a menu 316 related to the user can be displayed at the top of the user interface. The first banner 302 can be configured to display data for a location 306 selected from a drop down menu 304 related to the user. Only locations associated with the user via the user profile can be displayed.

Notifications of patients with outstanding encounters 320 can be displayed on the user interface 300. The notification can include patient information 322, including the patient's name, gender, age, birthdate, and other relevant patient information. At least a portion of the patient profile 330 can also be displayed on the user interface 300, along with a portion of the patient information 332, an encounter indicator 334, location-related information 338, and a summary of the patient's condition with a follow-up task listing 338 for display on the user device.

Figure 4:
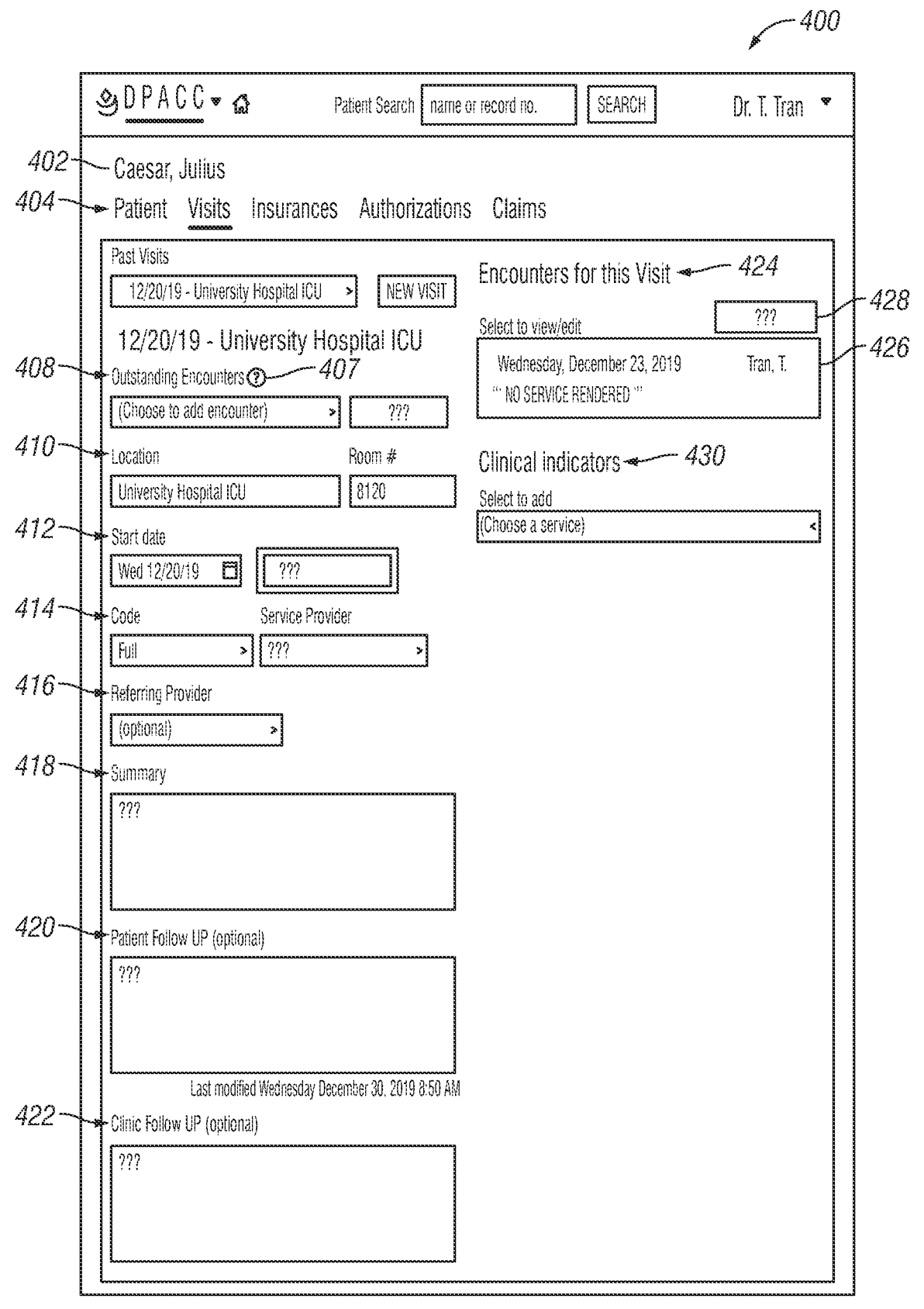

FIG. 4 illustrates a view of a patient profile 400, in accordance with one exemplary embodiment of the present disclosure. The patient profile 400 can receive data from the UI module 220 to access and display data from any module of CCS 102, including the patient interaction module 210, profile module 218, and notification module 214. The patient profile includes the patient name 402, patient-related navigation 404, and a user interface 406 for selecting, viewing, and modifying patient profile data. Navigation tools are provided to be able to review patient-related data for past visits, outstanding encounters 408, location 410, start date 412, code 414, referring provider 416, encounter summary 418, in-patient follow-up 420, clinic follow-up 422, encounters for this visit 424, encounter selection 426, add encounter 428, and clinical indicators 430.

Figure 5:
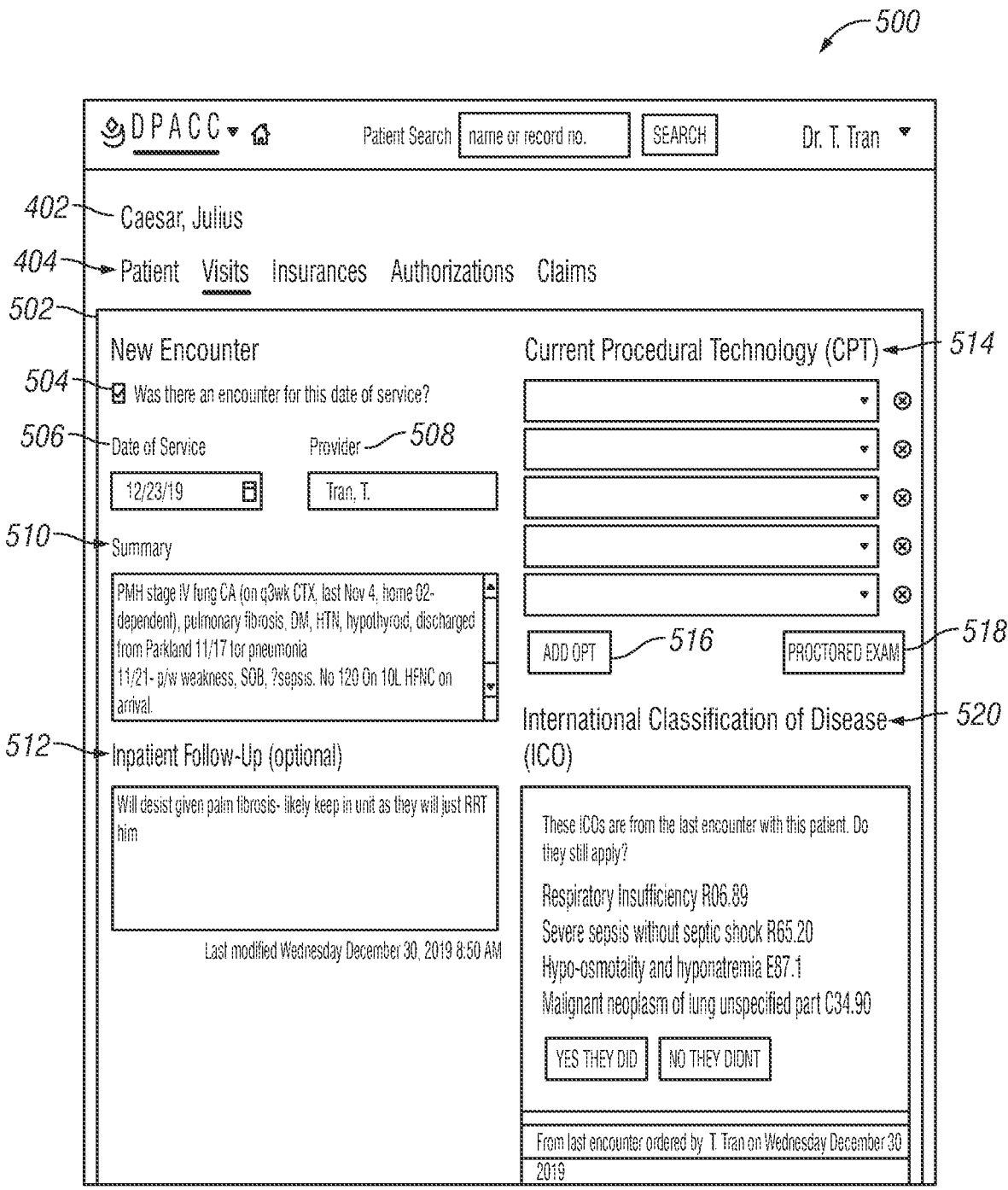
FIG. 5 illustrates a user interface related to provider charge capture, in accordance with one exemplary embodiment of the present disclosure.

FIG. 5 illustrates a user interface related to provider charge capture 500, in accordance with one exemplary embodiment of the present disclosure. The charge capture user interface 500 can receive data from the UI module 220 to access and display data from any module of CCS 102, including the charge module 212, patient interaction module 210, profile module 218, and notification module 214. The provider charge capture interface 500 includes the patient name 402, patient-related navigation 404, and a user interface 502 for selecting, viewing, and modifying information related to a new patient encounter. The provider charge capture interface 500 further includes a selection element to indicate whether there was an encounter for a particular day of service 506, with the ability to designate a provider 508. Fields are provided to allow the user to enter an encounter summary 510 and in-patient follow-up 512. A CPT listing

514 indicates all CPTs for the encounter, with the ability to add an additional CPT 516 or add a proctored exam 518, wherein a user can identify which exam was proctored and by whom, on which date. An ICD listing 520 indicates all ICDs for the encounter, with the ability to add an additional ICDs. For ease of facilitation, the user is prompted whether ICDs from the last encounter with a patient still apply, such that this ICDs will be imported for the instant encounter, saving the provider from wasted time from entering repeat ICD codes. The charge capture user interface 500 can access the previous ICD codes via the profile module 218.

Figure 6:
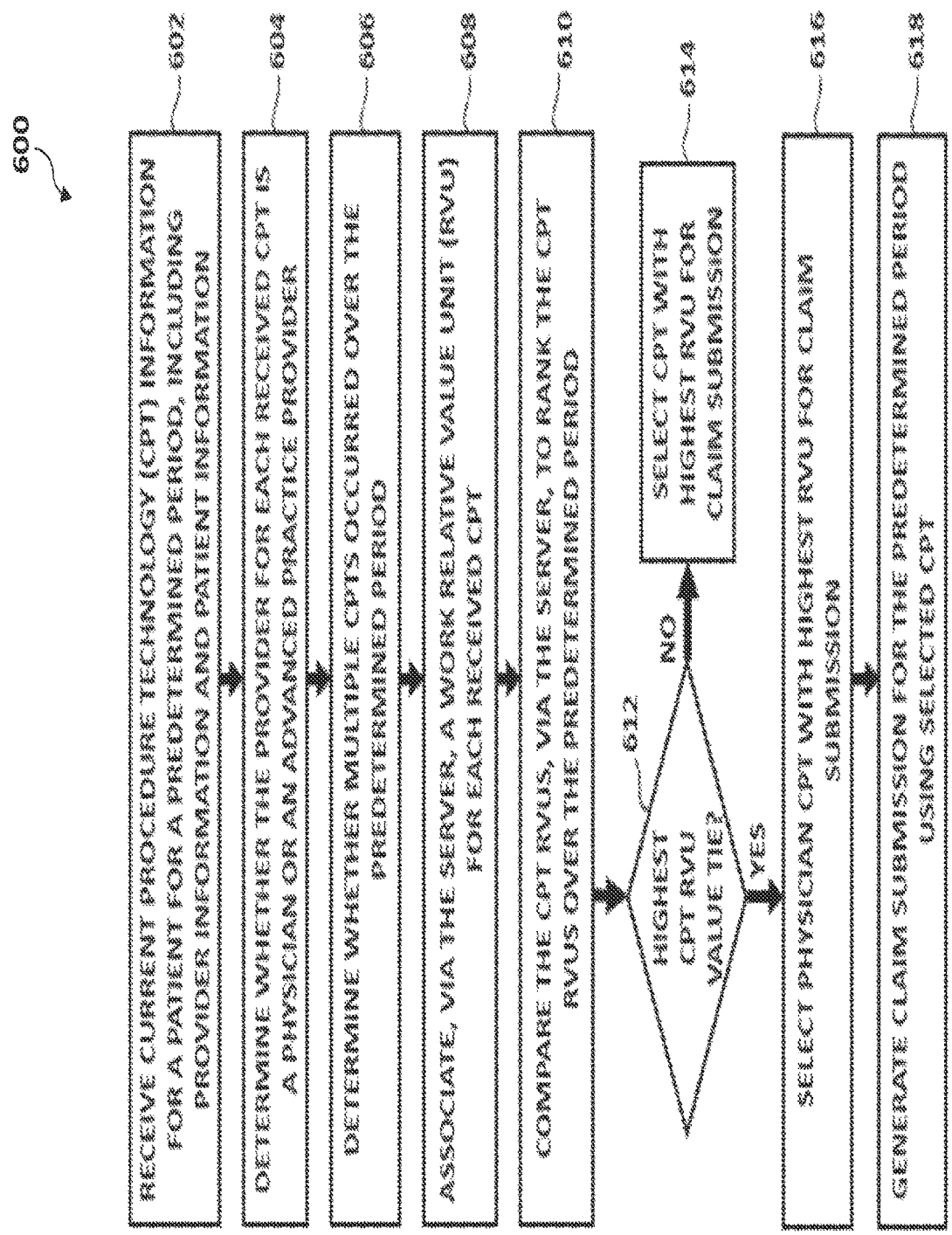
FIG. 6 illustrates a flow chart diagram for prioritizing a Current Procedural Technology (CPT) code, in accordance with one exemplary embodiment of the present disclosure.

FIG. 6 illustrates a flow chart diagram 600 exemplifying control logic embodying features of a method for prioritizing a Current Procedural Technology (CPT) code, in accordance with one exemplary embodiment of the present disclosure. The CPT code prioritization control logic 600 can be implemented as an algorithm on a server, a machine learning module, or other suitable system. The CPT code prioritization control logic 600 can be achieved with software, hardware, an application programming interface (API), a network connection, a network transfer protocol, HTML, DHTML, JavaScript, Dojo, Ruby, Rails, other suitable applications, or a suitable combinations thereof.

The CPT code prioritization control logic 600 can leverage the ability of a computer platform to spawn multiple processes and threads by processing data simultaneously. The speed and efficiency of the CPT code prioritization control logic 600 is greatly improved by instantiating more than one process to generate a record having a patient's data. However, one skilled in the art of programming will appreciate that use of a single processing thread may also be utilized and is within the scope of the present invention.

The CPT code prioritization control logic 600 process flow of the present embodiment begins at step 602, where the control logic can receive Current Procedure Technology (CPT) information for a patient for a predetermined period, including provider information and patient information. The CPT information can be received from the CCS 102, memory 222, an EHR/EMR system 108, web portal, or other suitable mechanism. One or more CPTs can be received for one or more patients. The predetermined period of time is preferably a 24-hour period, but can be changed to any suitable period, as requested by the user. The CPT information can include CPT codes, patient information, profile information, or other suitable information. The control logic then proceeds to step 604.

At step 604, the CPT code prioritization control logic 600 can determine whether the provider for each received CPT is a Physician or an Advanced Practice Provider. The CPT code prioritization control logic 600 can access the provider profile to determine the type of provider, among other profile information, via an encrypted network connection, or other suitable means. The control logic then proceeds to step 606.

At step 606, the CPT code prioritization control logic 600 can determine whether multiple CPTs occurred over the predetermined period. If a single CPT occurred over the predetermined period, the control logic can select the single CPT for claim submission and proceed to step 618. However, should multiple CPTs be detected, the CPT code prioritization control logic 600 can search for Work Relative Value Unit (RVU) for each received CPT. For example, certain insurers or programs utilize a physician fee schedule to determine claim payments for provider services. The fee for each service can depend on RVUs, which rank the resources used to provide each service. These resources can include the physician's work, the expenses of the physician's practice, and professional liability insurance. The RVU can be generated and stored locally in a database in the memory 222, or can be accessed at an external system 202 via the Internet 204. The CPT RVU database can be accessed via a local are network, wide area network, application programming interface, or other suitable communication mechanism. The control logic then proceeds to step 608.

At step 608, the CPT code prioritization control logic 600 can associate, via the server, a Work Relative Value Unit (RVU) for each received CPT. The CPT code prioritization control logic 600 can edit the RVUs to account for certain factors associated with the CPT. Although physician CPTs typically have a greater RVU, given the type of procedure or the specialization, among other factors, the APP CPT may have a greater RVU. Any edits can be documented in the CCS 102 for auditing purposes. As each CPT has been assigned an RVU, the RVUs and associated CPTs can be ranked. The control logic then proceeds to step 610.

At step 610, the CPT code prioritization control logic 600 can compare the CPT RVUs, via the server, to rank the CPT RVUs over the predetermined period. The RVUs can be sorted according to sequential search, bubble search, or quick search algorithms, among others. The control logic then proceeds to step 612.

At step 612, the CPT code prioritization control logic 600 can determine whether there is a tie for the highest RVU among CPTs. From time-to-time, two or more CPTs can be assigned the same RVU. If there is a tie between two or more CPTs for the highest RVU, the control logic then proceeds to step 616. If there is not a tie between two or more CPTs for the highest RVU, the control logic then proceeds to step 616.

At step 614, the CPT code prioritization control logic 600 can select the CPT with highest RVU for claim submission. The selection can include flagging the selected CPT, storing the CPT in RAM, or otherwise designating the CPT as selected. The control logic then proceeds to step 618.

At step 616, the CPT code prioritization control logic 600 can select a physician CPT with highest RVU for claim submission. Typically, physician CPTs can be billed at a higher rate than APP CPTs, as such, the physician CPT is prioritized over the APP CPT. Should no physician CPT exist among the tied CPTs, any APP CPT can be selected. Similarly, if only physician CPTs exist among the tied CPTs, any physician CPT can be selected. The selection can include flagging the selected CPT, storing the CPT in RAM, or otherwise designating the CPT as selected. The control logic then proceeds to step 618.

At step 618, the CPT code prioritization control logic 600 can generate, via the server, a claim submission for the predetermined period using the selected CPT. The claim can formatted in an ANSI-X12 837 file format, or other suitable format. The control logic then terminates or awaits a new CPT information and can repeat the aforementioned steps.

Figure 7:
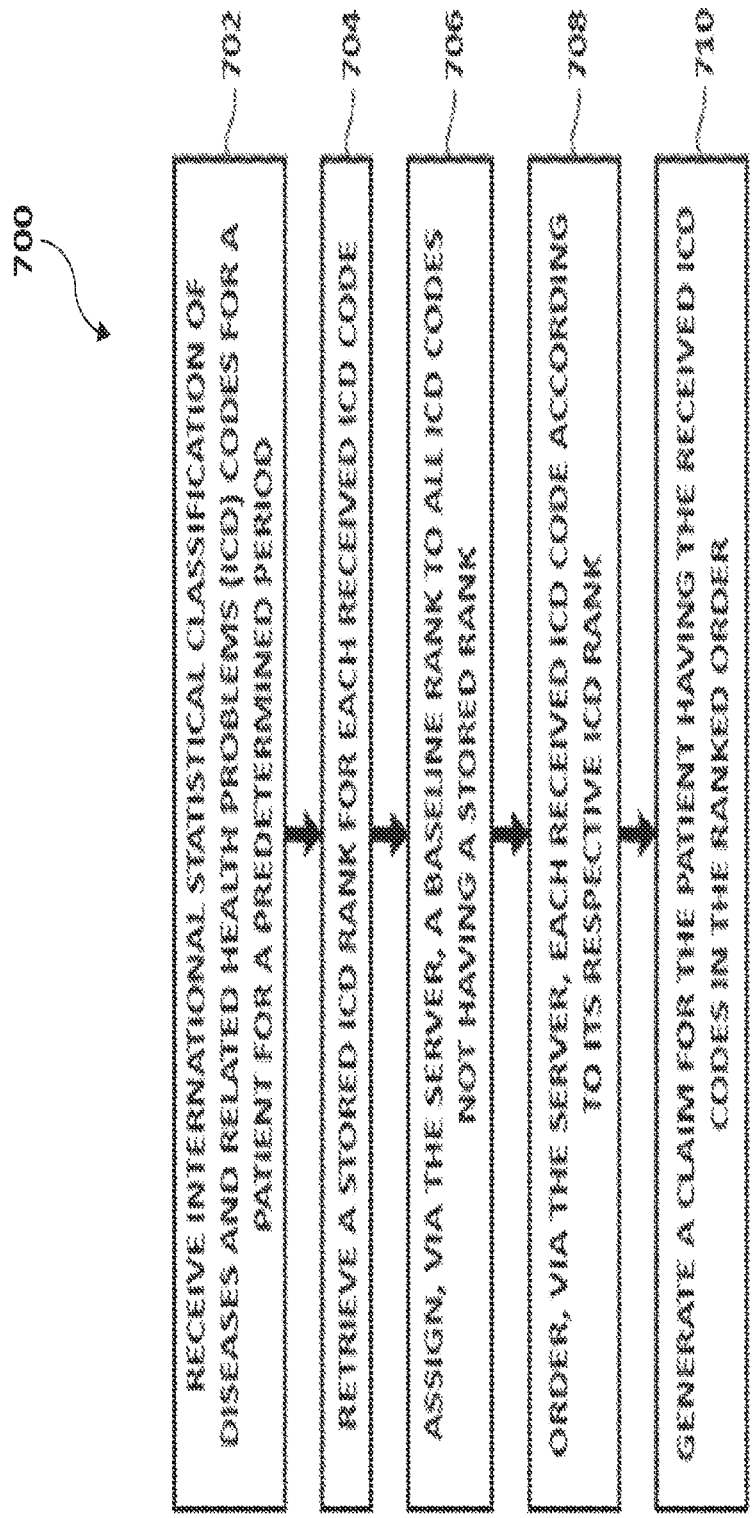
FIG. 7 illustrates a flow chart diagram for prioritizing an International Statistical Classification of Diseases and Related Health Problems (ICD) code, in accordance with one exemplary embodiment of the present disclosure.

FIG. 7 illustrates a flow chart diagram 700 exemplifying control logic embodying features of a method for prioritizing an International Statistical Classification of Diseases and Related Health Problems (ICD) code, in accordance with one exemplary embodiment of the present disclosure. The ICD code prioritization control logic 700 can be implemented as an algorithm on a server, a machine learning module, or other suitable system. The ICD code prioritization control logic 700 can be achieved with software, hardware, an application programming interface (API), a network connection, a network transfer protocol, HTML, DHTML, JavaScript, Dojo, Ruby, Rails, other suitable applications, or a suitable combinations thereof.

The ICD code prioritization control logic 700 can leverage the ability of a computer platform to spawn multiple processes and threads by processing data simultaneously. The speed and efficiency of the ICD code prioritization control logic 700 is greatly improved by instantiating more than one process to generate a record having a patient's data. However, one skilled in the art of programming will appreciate that use of a single processing thread may also be utilized and is within the scope of the present invention.

The ICD code prioritization control logic 700 process flow of the present embodiment begins at step 702, where the control logic can receive International Statistical Classification of Diseases and Related Health Problems (ICD) information for a patient, for a predetermined period, including provider information and patient information. The ICD information can be received from the CCS 102, memory 222, an EHR/EMR system 108, web portal, or other suitable mechanism. One or more ICDs can be received for one or more patients. The predetermined period of time is preferably a 24-hour period, but can be changed to any suitable period, as requested by the user. The ICD information can include ICD codes, patient information, profile information, or other suitable information. The control logic then proceeds to step 704.

At step 704, the ICD code prioritization control logic 700 can retrieve a stored ICD rank for each received ICD code. If a particular ICD code was previously submitted in a claim using the CCS 102, the ICD code can be assigned a rank based upon whether the ICD code was accepted or denied. The ICD rank can be generated and stored locally in a database in the memory 222, or can be accessed at an external system 202 via the Internet 204. For example, the CCS 102 can generate an ICD rank for each ICD code submitted in a claim. In one exemplary embodiment, the rankings can range in value from 1 to 100. Alternatively, the rankings can range between 1 and 5, or any other suitable values. The ICD ranking database can be accessed via a local area network, wide area network, application programming interface, or other suitable communication mechanism. The control logic then proceeds to step 706.

At step 706, the ICD code prioritization control logic 700 can assign and store, via the server, a baseline rank for all ICD codes not having a stored rank. If an ICD code was not previously submitted by the CCS 102, it may not have a rank associated with the ICD code. ICD codes that are to be submitted for a first time can be assigned a baseline rank. In one exemplary embodiment, the baseline rank can be 50, however any value in the middle of the selected ranking range can be suitable as the baseline rank. The newly assigned rank can be stored in the ICD ranking database, or other suitable storage location. The control logic then proceeds to step 708.

At step 708, the ICD code prioritization control logic 700 can order, via the server, each received ICD code according to its respective ICD rank. ICD codes that were previously accepted will have a higher ranking than ICD codes that were previously rejected. As the order in which the ICD codes are presented to the payer matter, the ICD code prioritization control logic 700 can rearrange the ICD codes in a claim, placing the codes that are most likely to be accepted at the beginning of the list of ICD codes in the claim. The ICDs can be ordered according to sequential search, bubble search, or quick search algorithms, among others. The control logic then proceeds to step 710.

Figure 8:
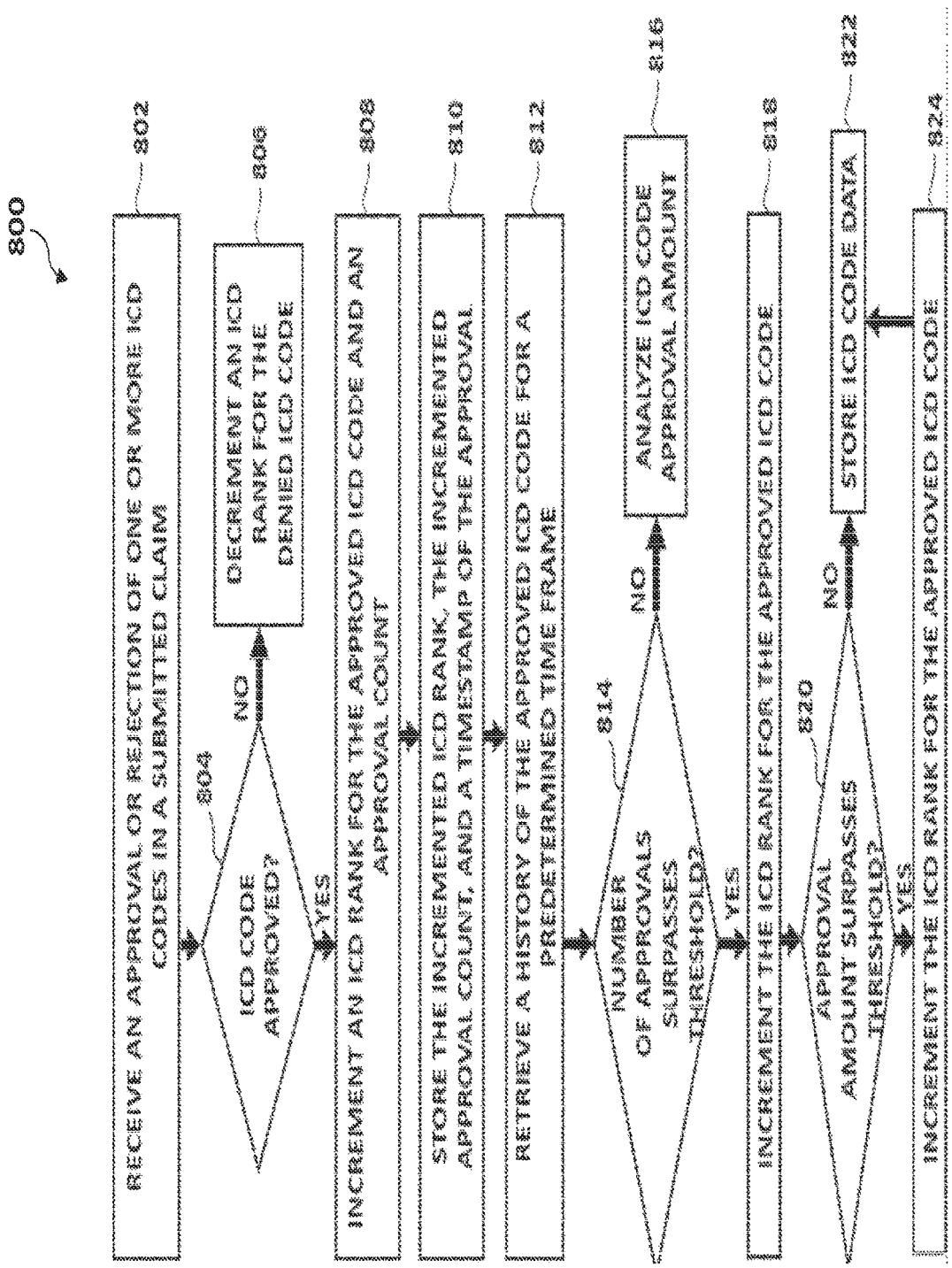
FIG. 8 illustrates a flow chart diagram for assigning a prioritization ranking of an ICD code, in accordance with one exemplary embodiment of the present disclosure.

At step 710, the ICD code prioritization control logic 700 can generate a claim for the patient having the received ICD codes in the ranked order. The claim can formatted in an ANSI-X12 837 file format, or other suitable format. The control logic then terminates or awaits a new ICD information and can repeat the aforementioned steps, FIG. 8 illustrates a flow chart diagram 800 exemplifying control logic embodying features of a method for assigning a prioritization ranking of an ICD code, in accordance with one exemplary embodiment of the present disclosure. The ICD ranking control logic 800 can be implemented as an algorithm on a server, a machine learning module, or other suitable system. The ICD ranking control logic 800 can be achieved with software, hardware, an application programming interface (API), a network connection, a network transfer protocol, HTML, DHTML, JavaScript, Dojo, Ruby, Rails, other suitable applications, or a suitable combinations thereof.

The ICD ranking control logic 800 can leverage the ability of a computer platform to spawn multiple processes and threads by processing data simultaneously. The speed and efficiency of the ICD ranking control logic 800 is greatly improved by instantiating more than one process to generate a record having a patient's data. However, one skilled in the art of programming will appreciate that use of a single processing thread may also be utilized and is within the scope of the present invention.

The ICD ranking control logic 800 process flow of the present embodiment begins at step 802, where the control logic can receive an approval or rejection of one or more ICD codes in a submitted claim. After the CCS 102 submits a claim to the claims management system 104, the claims management system 104 can respond by providing an approval, partial approval, or a rejection of the claim. The control logic then proceeds to step 804.

At step 804, the ICD ranking control logic 800 can determine whether the submitted ICD code was approved or rejected. If the submitted ICD code was approved, the control logic then proceeds to step 808. If the submitted ICD code was denied, the control logic then proceeds to step 806.

At step 806, the ICD ranking control logic 800 can, via the server, decrement an CD rank for a denied ICD code and increment a denial count for the denied ICD code. In one exemplary embodiment, the ICD ranking for a denied ICD code can be decremented by 10 units, however, any suitable decrement amount can be used. The denial count can be a counter or other suitable mechanism for storing the number of denials associated with the denied ICD code. The control logic then proceeds to step 810.

At step 808, the ICD ranking control logic 800 can, via the server, increment an ICD rank for the approved ICD code and increment an approval count for the approved ICD code. In one exemplary embodiment, the ICD ranking for an approved ICD code can be incremented by 10 units, however, any suitable increment amount can be used. The approval count can be a counter or other suitable mechanism for storing the number of approvals associated with the approved ICD code. The control logic then proceeds to step 810.

At step 810, the ICD ranking control logic 800 can store the incremented ICD rank, the incremented approval count, and a timestamp of the received approval. Additionally, the ICD ranking control logic 800 can store the decremented ICD rank, the incremented denial count, and a timestamp of the received denial. The control logic then proceeds to step 812.

At step 812, the ICD ranking control logic 800 can retrieve a history of the approved or denied ICD code for a predetermined time frame. The history can include the incremented/decremented ICD rank, the incremented approval/denial count, the payment amounts, and a timestamp of the received approval/denial, among other information. Certain conditions can be preferentially paid, if, for example, a certain number of approvals are granted for a particular ICD code within a shortened predetermined time frame, or if the ICD code is paid out at a higher amount. The ICD code history can be utilized by the CCS 102 to analyze the metrics of the ICD code to determine whether to increment or decrement its ICD rank. The control logic then proceeds to step 814.

At step 814, the ICD ranking control logic 800 can determine whether the number of ICD code claim approvals surpasses a first threshold. The ICD ranking control logic 800 can compare, via the server, the number of ICD code claim approvals with the first threshold to determine whether the threshold is surpassed. The ICD ranking control logic 800 can include a feedback loop such that the thresholds can be modified using other information. For example, the ICD ranking control logic 800 can calculate the differences, standard deviation, average, interpolation, or other data analysis, on the information to set or modify the thresholds. If the number of ICD code claim approvals surpasses a first threshold, the control logic then proceeds to step 818. If the number of ICD code claim approvals does not surpass the first threshold, the control logic then proceeds to step 816.

At step 816, the ICD ranking control logic 800 can, via the server, analyze the ICD Code approval amount. Each ICD code can be approved for a certain approval amount, in dollars or other suitable currency unit. The ICD ranking control logic 800 can compare the ICD Code approval amount of the approved claim with the approval amounts stored in the ICD code history. Alternatively, the ICD ranking control logic 800 can decrement the ICD rank for the approved/denied ICD code, should the number of denials exceed a certain threshold within the shortened predetermined time frame. In one exemplary embodiment, the ICD ranking for a denied ICD code can be decremented by 10 units, however, any suitable decrement amount can be used. The control logic then proceeds to step 820. In another exemplary embodiment, the ICD ranking for a denied ICD code can remain unchanged.

At step 818, the ICD ranking control logic 800 can, via the server, increment an ICD rank for the approved ICD code and increment an approval count for the approved ICD code. In one exemplary embodiment, the ICD ranking for an approved ICD code can be incremented by 10 units, however, any suitable increment amount can be used. The approval count can be a counter or other suitable mechanism for storing the number of approvals associated with the approved ICD code. The control logic then proceeds to step 820.

At step 820, the ICD ranking control logic 800 can determine whether the ICD code claim approval amount surpasses a second threshold. The ICD ranking control logic 800 can compare, via the server, the claim approval amounts of the approved ICD code claim with the second threshold to determine whether the second threshold is surpassed. The ICD ranking control logic 800 can include a feedback loop such that the thresholds can be modified using other information. For example, the ICD ranking control logic 800 can calculate the differences, standard deviation, average, interpolation, or other data analysis, on the information to set or modify the thresholds. If the approval amount of the ICD code claim surpasses the second threshold, the control logic then proceeds to step 824. If the approval amount of the ICD code claim does not surpass the second threshold, the control logic then proceeds to step 822.

At step 824, the ICD ranking control logic 800 can, via the server, increment an ICD rank for the approved ICD code and increment an approval count for the approved ICD code. In one exemplary embodiment, the ICD ranking for an approved ICD code can be incremented by 10 units, however, any suitable increment amount can be used. The approval count can be a counter or other suitable mechanism for storing the number of approvals associated with the approved ICD code. The control logic then proceeds to step 820.

At step 822, the ICD ranking control logic 800 can store the ICD code data for the approved ICD code. The ranking, approval amounts, thresholds, and other relevant information can be stored in the ICD code history. The control logic then proceeds to step 820.

The present disclosure achieves at least the following advantages:
1. Automatically optimizes the collections for the highest paid providers;
2. Provides a platform for providing easy and efficacious charge capture; and
3. Provides metrics that can point to higher patient care or areas for improvement.

Persons skilled in the art will readily understand that these advantages (as well as the advantages indicated in the summary) and objectives of this system would not be possible without the particular combination of computer hardware and other structural components and mechanisms assembled in this inventive system and described herein. It will be further understood that a variety of programming tools, known to persons skilled in the art, are available for implementing the control of the features and operations described in the foregoing material. Moreover, the particular choice of programming tool(s) may be governed by the specific objectives and constraints placed on the implementation plan selected for realizing the concepts set forth herein and in the appended claims.

The disclosure may be embodied in other specific forms without departing from the spirit or essential characteristics thereof. For example, each of the new structures described herein, may be modified to suit particular local variations or requirements while retaining their basic configurations or structural relationships with each other or while performing the same or similar functions described herein. The present embodiments are therefore to be considered in all respects as illustrative and not restrictive. Accordingly, the scope of the inventions are established by the appended claims rather than by the foregoing description. All changes which come within the meaning and range of equivalency of the claims are therefore intended to be embraced therein. Further, the individual elements of the claims are not well-understood, routine, or conventional. Instead, the claims are directed to the unconventional inventive concept described in the specification.

The invention claimed is:

1. An International Statistical Classification of Diseases and Related Health Problems (ICD) code prioritization system, comprising:
   a server having a system processor running a healthcare charge module configured to, in order to process and prioritize disease and related health problem codes, order and rank ICD codes by:
   receiving an approval or rejection of one or more ICD codes in a submitted claim;
   incrementing an ICD code rank for the approved ICD code and incrementing an approval count, if an ICD code is approved;

decrementing the ICD code rank for the denied ICD code and incrementing a denial count, if an ICD code is denied;

storing the ICD code rank, the incremented approval or denial count, and a timestamp of the approval or disapproval for the received approval or rejection;

creating a baseline rank for ICD codes not having a stored rank;

retrieving a history of approved ICD codes and denied ICD codes for a predetermined time frame;

ordering each ranked ICD code;

incrementing the ICD code rank for the approved ICD code, otherwise, analyzing the ICD code approval amount, if a number of approved ICD codes surpasses a first threshold;

decrementing the ICD code rank for a denied ICD code;

incrementing and storing the ICD code rank for an approved ICD code, otherwise, storing the ICD code rank, if the ICD code approval amount surpasses a second threshold;

decrementing and storing the ICD code rank for a denied ICD code, otherwise, storing the ICD code rank, if the ICD code is approved and under said second threshold or denied;

incrementing an ICD code rank for an approved ICD code and incrementing an approval count for the number of approved ICD codes;

generating a new claim based on each ICD code, incremented ICD codes, ranked ICD codes, ICD approval counts, ICD code approval amount, denied ICD codes, or a combination thereof, related to one or more procedures, diseases, related health problems, or a combination thereof; and submitting said claim to a payor for payment with an ordered rank of ICD codes prioritized highest to lowest increment or ranked order.

2. The International Statistical Classification of Diseases and Related Health Problems (ICD) code prioritization system of claim 1, wherein ICD history for an approved or denied ICD code may include incremented ICD rank, decremented ICD rank, incremented approval count, decremented denial count, ICD code-related payment amount, timestamped approval or denial, or a combination thereof.

3. The International Statistical Classification of Diseases and Related Health Problems (ICD) code prioritization system of claim 2 wherein if an ICD code is approved, an ICD rank is incremented for the approved ICD code and an approval count is tallied and incremented, if an ICD code is denied, the ICD rank is decremented for the denied ICD code and a denial count is tallied and decremented which is then stored to a memory.

4. The International Statistical Classification of Diseases and Related Health Problems (ICD) code prioritization system of claim 1, wherein ICD code prioritization control logic is implemented as an algorithm on a server, a machine learning module, or other suitable system, and achieved with software, hardware, an application programming interface (API), a network connection, a network transfer protocol, HTML, DHTML, JavaScript, Dojo, Ruby, Rails, other applications, or a combination thereof.

5. The International Statistical Classification of Diseases and Related Health Problems (ICD) code prioritization system of claim 4, wherein said control logic leverages the ability of a computer platform to utilize a single processing thread or spawn multiple processes and threads by processing data simultaneously through two to a plurality of processes for two to a plurality of patients.

6. The International Statistical Classification of Diseases and Related Health Problems (ICD) code prioritization system of claim 1, wherein said predetermined timeframe may be periodic or aperiodic.

7. The International Statistical Classification of Diseases and Related Health Problems (ICD) code prioritization system of claim 5, wherein those ICD codes not having a stored rank or not previously being submitted to said system's control logic are assigned said baseline rank.

8. The International Statistical Classification of Diseases and Related Health Problems (ICD) code prioritization system of claim 7, wherein stored ranked ICD codes and non-stored, non-ranked ICD codes are arranged and ranked by said control logic according to those most likely to be accepted by a payor based on ICD code rank, ICD code incremented count, ICD code decremented count, ICD code approval amount, or a combination thereof.

9. The International Statistical Classification of Diseases and Related Health Problems (ICD) code prioritization system of claim 2, wherein control logic ranked ICD code payment amounts are prioritized as charge entries for a given encounter or procedure whereby ICD prioritization and Current Procedural Technology (CPT) codes are determined algorithmically to determine efficiency metrics and payor reimbursements.

10. An International Statistical Classification of Diseases and Related Health Problems (ICD) code prioritization system, wherein control logic ranks ICD codes according to historical ICD codes, baseline ICD codes and work Relative Value unit (RVU) values by the following:

associating Current Procedural Technology (CPT) with a patient;

receiving Current Procedural Technology (CPT) information for said patient for a predetermined period, including provider information and patient information;

determining whether the provider for each received CPT is a physician or an advanced practice provider (APP);

determining whether multiple CPTs occurred over the predetermined period;

associating, via a server, said RVU with each received CPT;

comparing the CPT RVUs, via the server, to rank the CPT RVUs over the predetermined period;

generating a CPT RVU database;

selecting a physician CPT with the highest RVU for claim submission, if there is a tie for the highest CPT RVU value, otherwise, selecting a CPT with the highest RVU for claim submission;

generating a claim for the predetermined period using the selected CPT code or codes; and submitting to a payor a claim for said selected CPT code or codes.

11. The International Statistical Classification of Diseases and Related Health Problems (ICD) code prioritization system of claim 10, wherein, if two to a plurality of CPTs are detected over a predetermined period, said control logic operates by:

searching for work relative value units (RVUs) for each CPT to create a CPT RVU database for CPT code prioritization.

12. The International Statistical Classification of Diseases and Related Health Problems (ICD) code prioritization system of claim 11, wherein fee for each service depends on RVUs and RVUs are calculated based on resources including: physicians' work, expenses of the physician's practice, and professional liability insurance.

13. The International Statistical Classification of Diseases and Related Health Problems (ICD) code prioritization system of claim 12, wherein RVUs are generated and stored locally in a database in a memory or are accessed from an external system via the Internet.

14. The International Statistical Classification of Diseases and Related Health Problems (ICD) code prioritization system of claim 13, wherein actual measured CPT and IDS ranking algorithms may be calculated and correlated with expected data.

15. The International Statistical Classification of Diseases and Related Health Problems (ICD) code prioritization system of claim 14, wherein ICD and CPT measured data may include time spent on each encounter/procedure, time spent between each encounter/procedure, or both, and expected data may be predetermined data stored in a memory including the designated time for each encounter/procedure, the designated time between each encounter/procedure, or both, which may be compared to determine efficiencies and inefficiencies.

16. The International Statistical Classification of Diseases and Related Health Problems (ICD) code prioritization system of claim 10, wherein the server calculates the differences, standard deviation, average, or interpolation of the information to set or modify first and second thresholds.

17. The International Statistical Classification of Diseases and Related Health Problems (ICD) code prioritization system of claim 11 wherein the CPT code prioritization control logic generates, via the server, a claim submission for the predetermined period using the selected CPT RVU or CPT RVUs.

\* \* \* \* \*